United States Patent
Mettler et al.

(10) Patent No.: US 10,668,425 B2
(45) Date of Patent: Jun. 2, 2020

(54) SEPARATION OF METHANE FROM GAS MIXTURES

(71) Applicant: ExxonMobil Research and Engineering Company, Annandale, NJ (US)

(72) Inventors: Matthew S. Mettler, Somerville, NJ (US); Ashish B. Mhadeshwar, Garnet Valley, PA (US); William R. Gunther, Clinton, NJ (US); Rustom M. Billimoria, Hellertown, PA (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 190 days.

(21) Appl. No.: 15/841,603

(22) Filed: Dec. 14, 2017

(65) Prior Publication Data

US 2018/0178157 A1    Jun. 28, 2018

Related U.S. Application Data

(60) Provisional application No. 62/437,726, filed on Dec. 22, 2016.

(51) Int. Cl.
| | |
|---|---|
| *B01D 47/02* | (2006.01) |
| *C07C 7/152* | (2006.01) |
| *C10L 3/10* | (2006.01) |
| *B01D 53/14* | (2006.01) |

(52) U.S. Cl.
CPC ....... *B01D 47/024* (2013.01); *B01D 53/1475* (2013.01); *C07C 7/152* (2013.01); *C10L 3/101* (2013.01); *B01D 2252/103* (2013.01); *B01D 2256/245* (2013.01); *B01D 2257/10* (2013.01); *B01D 2257/702* (2013.01); *C10L 2270/06* (2013.01); *C10L 2270/10* (2013.01); *Y02C 10/06* (2013.01); *Y02P 20/152* (2015.11)

(58) Field of Classification Search
None
See application file for complete search history.

(56) References Cited

U.S. PATENT DOCUMENTS

| | | | |
|---|---|---|---|
| 2,363,529 | A | 11/1944 | Hutchinson |
| 2,388,723 | A | 5/1946 | Crowther |
| 2,410,583 | A | 11/1946 | Hutchinson |
| 3,231,630 | A | 1/1966 | Glew |
| 5,434,330 | A | 7/1995 | Hnatow et al. |
| 6,028,234 | A | 2/2000 | Heinemann et al. |

(Continued)

FOREIGN PATENT DOCUMENTS

| | | |
|---|---|---|
| DE | 102011016742 A1 | 10/2012 |
| EP | 2564921 A1 | 3/2013 |

(Continued)

OTHER PUBLICATIONS

The International Search Report and Written Opinion of PCT/US2017/066319 dated Mar. 23, 2018.

(Continued)

*Primary Examiner* — Tam M Nguyen
(74) *Attorney, Agent, or Firm* — Priya G. Prasad

(57) ABSTRACT

Processes for separating methane from a gas mixture that comprises methane and $C_2$ gas, including $C_{2+}$ gas, and other gases, including $CO_2$ and $H_2S$, that are based upon formation of gas hydrates, and systems useful for implementing such processes, are disclosed.

17 Claims, 13 Drawing Sheets

(56) References Cited

U.S. PATENT DOCUMENTS

| | | |
|---|---|---|
| 6,111,155 A | 8/2000 | Williams et al. |
| 6,797,039 B2 | 9/2004 | Spencer |
| 8,633,004 B1 | 1/2014 | Rapp et al. |
| 2007/0248527 A1 | 10/2007 | Spencer |
| 2013/0012751 A1 | 1/2013 | Turner et al. |
| 2014/0262265 A1 | 9/2014 | Hutchins et al. |
| 2016/0184768 A1 | 6/2016 | Bagajewicz et al. |

FOREIGN PATENT DOCUMENTS

| | | |
|---|---|---|
| GB | 1167000 A | 10/1969 |
| WO | 20160037494 A1 | 3/2016 |

OTHER PUBLICATIONS

The International Search Report and Written Opinion of PCT/US2017/066279 dated Mar. 15, 2018.

Niaeiji et al., "Separation of methane-ethane gas mixtures via gas hydrate formation", Sep. Pur. Tech., 2014, 123, 139-144.

Qanbari et al., "Storage of $CO_2$ as hydrate beneath the ocean floor", Energy Procedia, 2011, 4, 3997-4004.

SEPARATION OF METHANE FROM GAS MIXTURES

CROSS-REFERENCE TO RELATED APPLICATIONS

This application claims the benefit of U.S. Provisional Application No. 62/437,726, filed on Dec. 22, 2016, the entire contents of which are incorporated herein by reference.

FIELD

This disclosure relates to separation of methane ($C_1$) from gas mixtures comprising ethane ($C_2$), or ethane and ethene, and sometimes gases containing these plus higher hydrocarbon gases, such as propane ($C_3$), n-butane, iso-butane ($C_4$), n-pentane, iso-pentane ($C_5$), as well as other gases, such as carbon dioxide ($CO_2$), nitrogen ($N_2$), hydrogen sulfide ($H_2S$), many of which are typical constituents of natural gas.

BACKGROUND

Separation of natural gas components is important for efficient utilization of natural gas feedstocks. $C_2$-$C_5$ hydrocarbons need to be removed from methane to (i) improve the heating value, (ii) sell the $C_2$-$C_5$ at a higher price as LNG or LPG, and (iii) make reactive molecules such as ethylene. At present, these hydrocarbons are separated by cryogenic distillation which is costly and energy intensive. Thus, there exists a need to develop an improved technology to separate, e.g. methane from $C_2$ or $C_{2+}$ gases in a cost effective and energy efficient manner.

U.S. Pat. No. 5,434,330 describes a process for separating clathrate forming gases by first contacting a gaseous stream with an aqueous solvent to form a hydrate suspension. The clathrate forming gases are then selectively recovered by exposing the hydrate suspension (or the separated hydrate) to increased temperature and/or reduced pressure.

US20130012751 describes a process by which the corrosive elements of a gas stream (e.g. $CO_2$, $H_2S$) can be separated from hydrocarbon gases in a hydrate-based separator using a similar approach as outlined in the U.S. Pat. No. 5,434,330. The process yields a gas product, e.g. a purified natural gas product, that is less corrosive due to removal of $H_2S$ and $CO_2$ from the natural gas.

SUMMARY

A hydrate-based separator offers significant reduction in energy and cost. Additionally, often natural gas contains a significant amount of $H_2S$ and $CO_2$ which are removed at the present state of the art by using adsorptive or other conventional techniques. For example, amine stripping of $CO_2$ is well-known. A hydrate-based separator can separate methane from $C_2$-$C_5$ hydrocarbons as well as from $H_2S$ and $CO_2$ in a single unit.

A system for separating methane from at least $C_2$ or $C_{2+}$ gases can include a hydrate formation reactor ("HFR"). The reactor can be operated in such a fashion that a feed gas stream comprising methane and $C_2$ or $C_{2+}$ gas and an aqueous phase stream are contacted in the reactor in a countercurrent flow. Disclosed is a technology based on hydrate-based gas separation in which $C_2$ or $C_{2+}$ gas is preferentially captured into a hydrate structure to selectively remove $C_2$ or $C_{2+}$ gas from a gas stream, such as a natural gas stream. The disclosed process and apparatus for implementing it provide improved separation of methane from $C_2$ or $C_{2+}$ gas and from mixed gases, such as produced natural gas or natural gas treated to remove corrosive gases, and improved energy and input material utilization. The ($C_2$ or) $C_{2+}$ gas-rich hydrate product of the process can be suitably stored or transported. Alternatively, the ($C_2$-rich or) $C_{2+}$ gas-rich hydrate product can be decomposed (before or after transport to another site) and the resulting ($C_2$-rich or) $C_{2+}$-rich gas can be used in subsequent industrial processes or burned for fuel. The methane-rich product gas can be transported for use in subsequent industrial processes or burned for fuel.

Thus, in one aspect, a system for separating methane from a gas mixture comprising ($C_2$ or) $C_{2+}$ or other gas, can include a hydrate formation reactor (HFR) that comprises an outer vessel configured:

with a plurality of stages arranged with a first stage proximal a first end of the vessel and second and any subsequent stages successively more proximal a second end of the vessel;

one or more gas feed inlets placed at a distance from the first end of the vessel the same as said distance of a stage that is a second or subsequent stage and configured to feed a gas stream into the vessel;

one or more aqueous phase inlets configured to feed an aqueous phase into the second end of the vessel or proximate thereto;

one or more hydrate slurry outlets configured to permit a draw off an aqueous phase hydrate slurry stream from the first end of the vessel or proximate thereto;

one or more gas product outlets configured to draw off a gas product stream from the second end of the vessel or proximate thereto; and a temperature control system effective to establish a temperature gradient or a series of temperature steps from a first temperature $T_1$ in a region proximate to the first end of the vessel to a second temperature $T_2$ in a region proximate to the second end of the vessel and controlling the temperature at each of the stages, wherein $T_1 > T_2$;

wherein the gas stream and the aqueous phase flow in a countercurrent manner through the vessel.

A gas feed to the hydrate formation reactor can include an inlet for adding a hydrate promoter to the gas feed. Such inlet for adding a hydrate promoter can include a mixer.

An aqueous phase inlet can be configured to input fresh aqueous phase into the HFR or to input recycled aqueous phase into the HFR. An aqueous phase inlet can be configured to include an inlet for adding a hydrate promoter to the aqueous phase. Such inlet for adding a hydrate promoter can include a mixer.

The methane separation system can further include a solid-liquid separator for separating an aqueous hydrate slurry drawn from the hydrate formation reactor into an aqueous phase product and a solid hydrate, and then can also include an aqueous phase recirculating line that feeds the aqueous phase product of the solid-liquid separator fully or partially into the second end of the vessel or proximate thereto. The aqueous phase recirculating line can include a cooling plant for cooling the aqueous phase liquid product prior to introducing the recirculated aqueous phase back into the hydrate formation reactor. The aqueous phase recirculating line can alternatively or additionally include an inlet for adding a hydrate promoter to the recirculating aqueous phase.

In a further aspect, the present disclosure provides a hydrate formation-based process for purifying methane from a gas comprising ($C_2$ or) $C_{2+}$ gases wherein the process comprises intimately contacting a feed gas stream comprising methane and $C_{2+}$ gases and a aqueous phase stream in a countercurrent flow to form a ($C_2$ gas-rich or) $C_{2+}$ gas-rich hydrate in the aqueous phase, a temperature $T_f$ being maintained at a gas feed stage f in the countercurrent flow, a temperature $T_2$ such that $T_2 < T_f$ being maintained at a stage n>f, and a temperature $T_1$ being maintained at a stage m≤f such that $T_1 \geq T_f$;

wherein:

$T_2$ is in the range from the incipient vapor formation temperature for ($C_2$ or) $C_{2+}$ gas to the incipient hydrate formation temperature for ($C_2$ or) $C_{2+}$ gas at the operating pressure of the process, and $T_1$ is a temperature at or below a temperature of convergence of the incipient ($C_2$ or) $C_{2+}$ hydrate formation and incipient ($C_2$ or) $C_{2+}$ vapor formation curves at the operating pressure of the process.

Typically, modestly high pressure operation, e.g. about 400 psia or above (depending on the composition of the input gas—for example for a produced natural gas), is required for effective separation of ($C_2$ or) $C_{2+}$ from methane in a hydrate formation-based process. Thus, one or more hydrate promoters can optionally be added to the gas feed stream of the process. Additionally or alternatively, one or more hydrate promoters can be added to the aqueous phase used in the process. These additives have the effect of lowering the pressure, or raising the temperature, at which the process can operate (thermodynamic hydrate promoters) or improving the kinetics of hydrate formation (kinetic hydrate promoters).

The ($C_2$-rich or) $C_{2+}$-rich hydrate product of the hydrate formation reactor can be transported as a source of ($C_2$ or) $C_{2+}$ to be used as fuel or as an input to an industrial process, or can be decomposed into a ($C_2$-rich or) $C_{2+}$-rich gas for use as fuel or input into other industrial processes.

The methane-rich gas product of the process obtained after separation of the gas stream from the aqueous phase can be stored at a pressure above atmospheric pressure, or transported directly from the hydrate formation reactor, to be used in other industrial processes or burned as fuel.

DETAILED DESCRIPTION

Definitions

Figure 1:
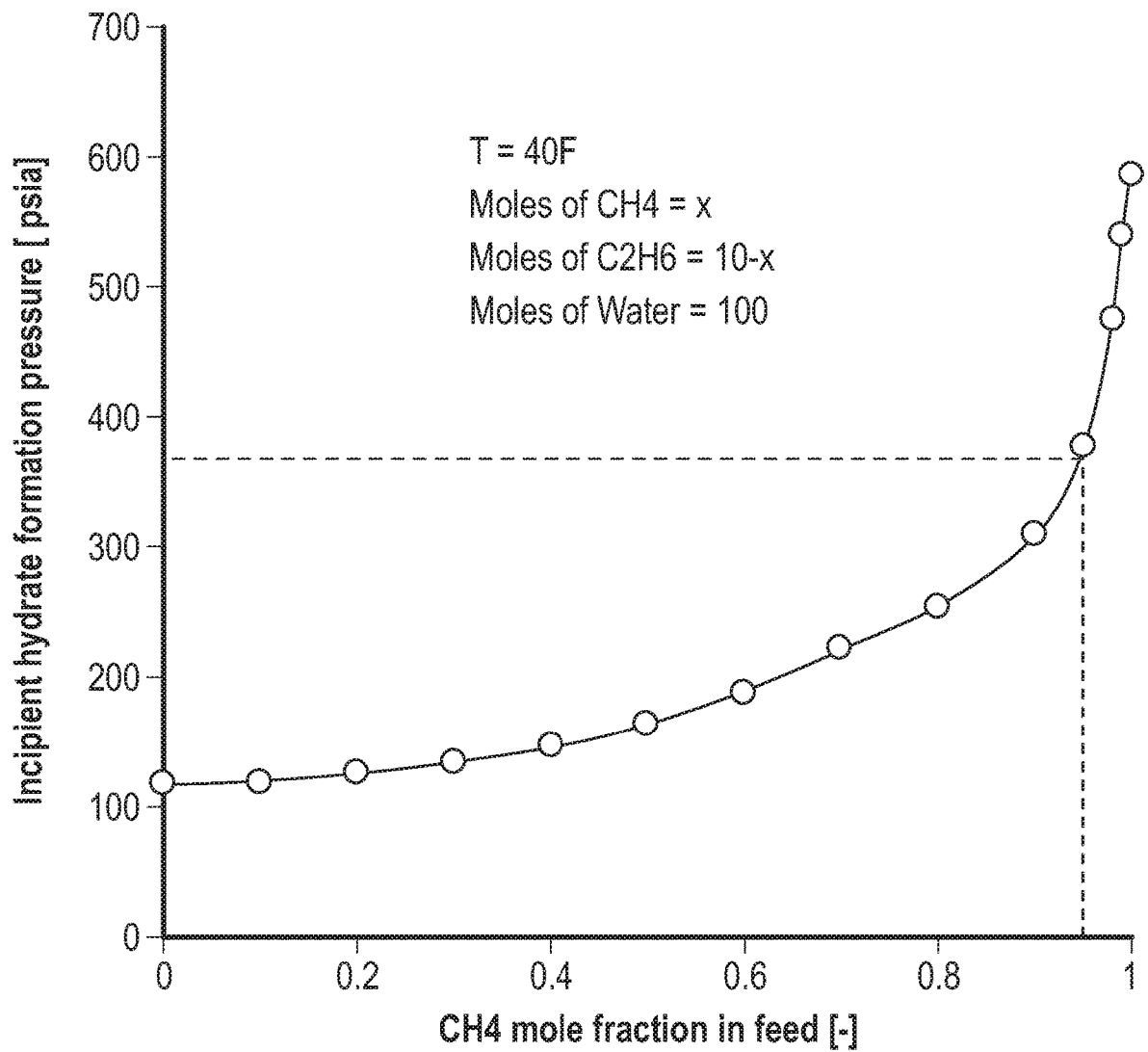
FIG. 1 is a graph of a methane-ethane hydrate formation phase diagram at 40° F.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments.

Accordingly, the apparatuses and processes encompassed are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

As used herein, "about" is a preposition describing some quantity or parameter value, and indicates that some variation around the stated amount or value is included. Generally, the degree of variation intended to be encompassed is that which would be understood by one of ordinary skill in the art not to materially affect the performance of an apparatus or device or a characteristic of a material or composition described by the amount or parameter. The degree of variation encompassed can be influenced by the ability of an artisan or ordinary skill to measure or control the amount or value in operation of a process or production of a substance or composition. In some instances, variation of up to 10% is envisioned. In some instances variation of up to 5% is envisioned. In some instances variation of up to 1% is envisioned. In some instances, variation of up to 0.5% is envisioned. In some instances, variation of up to 0.1% is envisioned. In the specific instance of the temperature of each stage of a HFR, "about" is intended to encompass 2-3% variation.

As used herein, an "aqueous phase" is water, a water solution of one or more dissolved substances, or either of these that includes a suspension of hydrate particles. The "dissolved substances" of a water solution can include molecules of gas partitioned into the aqueous phase from a gas being separated by the presently disclosed process. "Dissolved substances" can also include salts and organic molecules, either added to or originally present in the water forming the aqueous phase (for example substances present in seawater that might be used as the aqueous phase in some embodiments). "Dissolved substances" can also include thermodynamic hydrate promoters and kinetic hydrate promoters added to the aqueous phase. "Dissolved substances" can also include dissolved clathrates that have not agglomerated into substantial particles. "Hydrate particles" can include particles of sufficiently small size to remain suspended by flow of a slurry of the particles in the aqueous phase, and can also include aggregates of clathrate particles that have accreted to a size visible to the naked eye or larger, e.g. as to settle from a standing aqueous phase under the influence of gravity. Hydrate collected from disclosed processes and apparatus can be in solid form of substantial mass.

As used herein, "$C_2$" means ethane, or a mixture composed substantially of ethane and minor amounts of ethene. "$C_{2+}$" means a mixture of $C_2$ and higher hydrocarbons, for example $C_2$-$C_5$ hydrocarbons.

As used herein, a "clathrate" is a weak composite made of a host compound that forms a basic framework and a guest compound that is held in the host framework by intermolecular interaction, such as hydrogen bonding, Van der Waals forces, and the like. Clathrates may also be called "host-guest complexes", "inclusion compounds", and "adducts". As used herein, "clathrate" and "hydrate" are interchangeable terms used to indicate a clathrate having a basic framework made from water as the host compound. A hydrate is a crystalline solid which looks like ice, and forms when water molecules form a cage-like structure around a "hydrate-forming constituent."

Formation of a hydrate or clathrate is described herein as a "reaction", since a stable structure is formed (under appropriate conditions) from two previously separated compounds, although no chemical bonds are changed.

Figure 3:
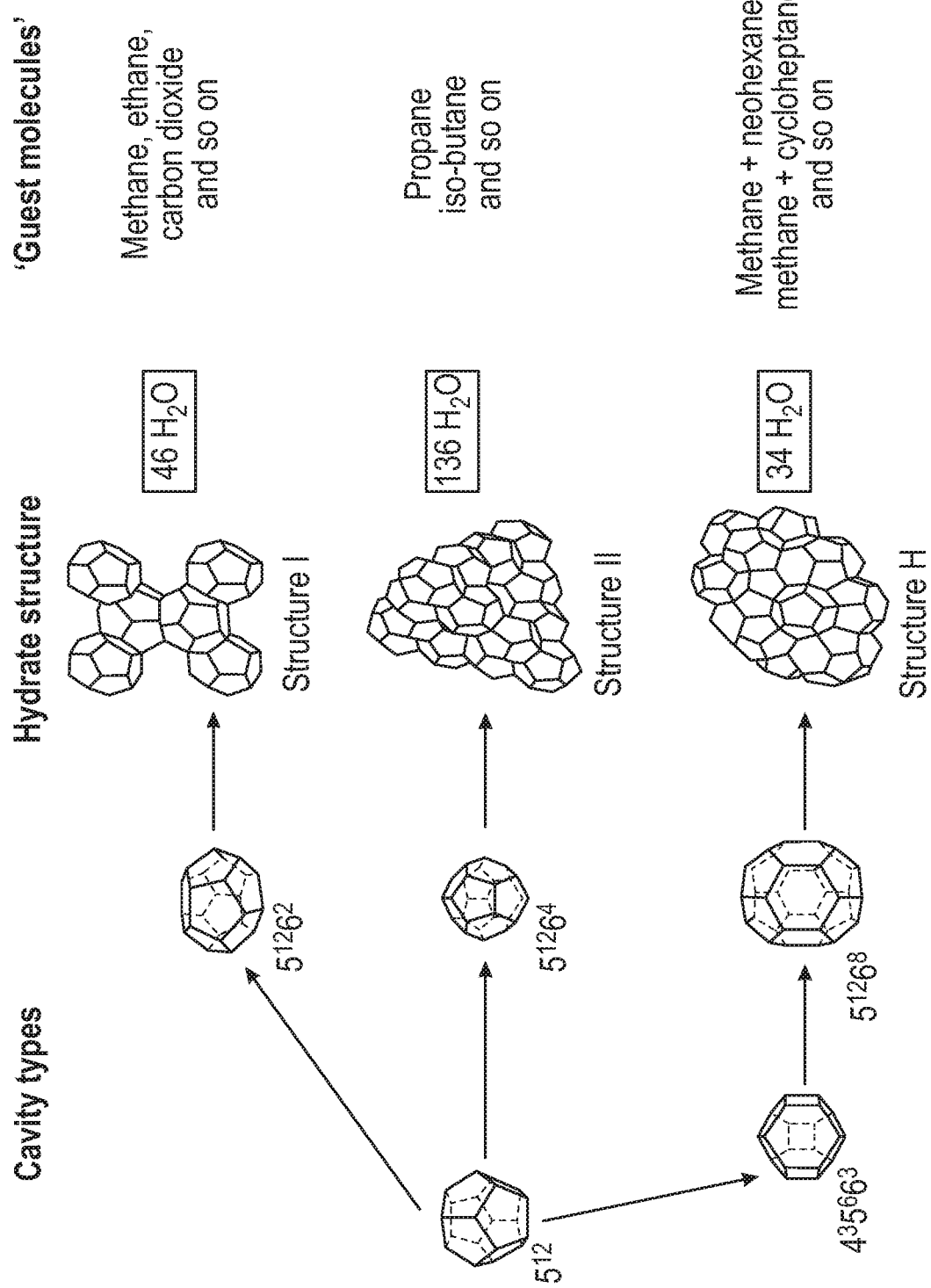
FIG. 3 illustrates various hydrate forms. (E. Dendy Sloan Jr., "Fundamental principles and applications of natural gas hydrates", *Nature*, vol. 426, p. 353 (2003).)

FIG. 3 shows some various framework structures of water-molecule clathrates and examples of molecular guests that can be found within them.

As used herein, a "hydrate-forming constituent" refers to a compound or molecule in a fluid, including natural gas, that forms hydrate at elevated pressures and/or reduced temperatures. Illustrative hydrate-forming constituents include hydrocarbons such as methane, ethane, propane, butane, neopentane, ethylene, propylene, isobutylene, cyclopropane, cyclobutane, cyclopentane, cyclohexane, and benzene. Hydrate-forming constituents can also include non-hydrocarbons, such as oxygen, nitrogen, hydrogen sulfide, carbon dioxide, sulfur dioxide, and chlorine.

As used herein, a "compressor" is a machine that increases the pressure of a gas by the application of work (compression). Accordingly, a low pressure gas (for example, at 5 psig) may be compressed into a high-pressure gas (for example, at 1000 psig) for transmission through a pipeline, injection into a well, or other processes.

As used herein, a "column", "tower" or "reactor" means a fractionation column or zone, i.e., a contacting column or zone, wherein liquid and vapor phases can be countercurrently contacted to effect separation of compounds in a mixture of phases. For example, a separation in a vapor-liquid-hydrate system may be performed by contacting of the vapor and liquid phases (which can include hydrate under appropriate conditions) on a series of vertically spaced trays or plates mounted within a column and/or on packing elements such as structured or random packing. Further, a separation of compounds in a mixture of solid, liquid, and vapor phases may be effected by a contacting countercurrent flow of the solid and/or liquid phases (which may contain hydrate) in an opposite direction to a vapor phase.

As used herein, the term "gas" is used interchangeably with "vapor," and means a substance or mixture of substances in the gaseous state as distinguished from the liquid or solid state. Likewise, the term "liquid" means a substance or mixture of substances in the liquid state as distinguished from the gas or solid state. As used herein, "fluid" is a generic term that may include either a gas or vapor.

As used herein, "kinetic hydrate promoter" ("KHP") refers to a molecule and/or compound or mixture of molecules and/or compounds capable of increasing the rate of hydrate formation in a fluid that is either liquid or gas phase. A kinetic hydrate promoter can be a solid or liquid at room temperature and/or operating conditions.

As used herein, the term "minimum effective operating pressure" refers to the pressure below which hydrates do not form in fluids containing hydrate forming constituents during the time the fluids are resident in a vessel or line.

As used herein, the term "maximum effective operating temperature" refers to the temperature above which hydrates do not form in fluids containing hydrate forming constituents during the time the fluids are resident in a vessel or line. For thermodynamic promotion of hydrate formation only, the maximum effective operating temperature is higher than the maximum effective operating temperature in the absence of the addition of a THP. When a kinetic hydrate promoter is added together with a THP, the maximum effective operating temperature is typically higher than the thermodynamically promoted hydrate formation temperature.

As used herein, a "McCabe-Thiele plot" is a graph of an equilibrium concentration between two chemical components showing the concentration ratio of the components in each of two phases. In the graph, operating lines are used to define the mass balance relationships between the components. A McCabe-Thiele plot can be used to design a separation system based on the different concentrations of each of the components in each of the different phases. While McCabe-Thiele plots are generally used to design distillation columns based on vapor-liquid equilibriums, they can be applied to separations base on any phase equilibrium, such as the clathrate-liquid equilibrium discussed herein.

Construction of a McCabe-Thiele plot from equilibrium calculations is considered to be within the skill of the ordinary artisan. A vapor-liquid equilibrium curve can be constructed from a mixture phase diagram. (W. L. McCabe & E. W. Thiele, *Industrial and Engineering Chemistry, vol.*, pp. 605-611 (1925).—see also https://en.wikipedia.org/wiki/McCabe%E2%80%93Thiele_method.)

As used herein, a "plant" is a known apparatus or a collection of known apparatuses operably connected to perform a stated function. For example, a "cooling plant" will include equipment for chilling of a liquid passing through the cooling plant. A "facility" is a collection of plants that together accomplish one or more functions. In its broadest sense, the term plant is applied to any equipment that may be present along a flow path of a system as disclosed herein.

As used herein, "pressure" is the force exerted per unit area by the gas on walls enclosing a volume. Pressure can be shown as pounds per square inch (psi). "Atmospheric pressure" refers to the local pressure of the air. "Absolute pressure" (psia) refers to the sum of the atmospheric pressure (14.7 psia at standard conditions) plus the gage pressure (psig). "Gauge pressure" (psig) refers to the pressure measured by a gauge, which indicates only the pressure exceeding the local atmospheric pressure (i.e., a gauge pressure of 0 psig corresponds to an absolute pressure of 14.7 psia). The term "vapor pressure" has the usual thermodynamic meaning. For a pure component in an enclosed system at a given pressure, the component vapor pressure is essentially equal to the total pressure in the system.

As used herein, the terms "produced" (e.g. fluids or e.g. natural gas) refers to liquids or gases removed from a subsurface geologic formation. Such produced fluids may include liquids (such as oil or water) and gases, such as natural gas (comprising e.g. $C_{2+}$ gas and perhaps water (liquid and/or vapor), $CO_2$, and $H_2S$), among others.

As used herein, a "stage" in a column or reactor is a zone of controlled temperature within the reactor. The temperature to be set at each stage in the reactor can be determined by calculating phase diagrams for vapor-liquid (v-l), vapor-liquid-hydrate (v-l-h) and liquid-hydrate (l-h) phase diagrams for a feed gas composition, of the two gases to be separated (methane and ethane, for example, as below) for mol % of one of the gases to be separated from the feed vs. temperature at a given pressure. A temperature for the first stage can be selected by picking a temperature between the equilibrium incipient hydrate curve and incipient vapor curve at the composition desired in the hydrate phase. A temperature of the last stage is selected by picking the temperature on the incipient vapor curve at the composition desired in the gas phase. Temperatures of intermediate phases, if any, are identified by noting the composition of the incipient vapor at the temperature selected for the first stage, then noting the temperature of the incipient hydrate curve at this composition as the temperature for the second stage. The temperature of the third stage is selected by noting the composition at the incipient vapor curve at the temperature of the second stage, then noting the temperature of the incipient hydrate curve at this composition, etc.

Stages in a hydrate formation reactor are implemented by establishing a zone of controlled temperature at a particular section of a hydrate forming reactor, as described further below.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, "thermodynamic hydrate promoter" (THP) refers to a molecule and/or compound, or mixture of molecules and/or compounds capable of reducing the hydrate formation pressure (at a given temperature) in a fluid that is either liquid or gas phase. The addition of a THP to the fluid also has the effect of raising the temperature at which hydrates form at a given pressure.

A system for separation of methane from ($C_2$ or) $C_{2+}$ gases from natural gas or other gas mixtures includes a hydrate formation reactor in which ($C_2$ or) $C_{2+}$ gases from the gas mixture are partitioned into a hydrate phase by a countercurrent flow against an aqueous phase. The hydrate formation reactor comprises an outer vessel configured:

with a plurality of stages arranged with a first stage proximal a first end of the vessel and second and any subsequent stages successively more proximal a second end of the vessel;

one or more gas feed inlets placed at a distance distal from the first end of the vessel the same as said distance of a stage that is a second or subsequent stage and configured to feed a gas stream into the vessel;

one or more aqueous phase inlets configured to feed an aqueous phase into the second end of the vessel or proximate thereto;

one or more hydrate slurry outlets configured to draw off a hydrate slurry stream from the first end of the vessel or proximate thereto;

one or more gas product outlets configured to draw off a gas product stream from the second end of the vessel or proximate thereto; and a temperature control system effective to establish a temperature gradient or a series of temperature steps from a first temperature T1 in a region proximate to the first end of the vessel to a second temperature T2 in a region proximate to the second end of the vessel, and controlling the temperature at each of the stages, wherein $T_1 > T_2$;

wherein the gas stream and the aqueous phase flow in a countercurrent manner through the vessel.

The hydrate forming reactor accomplishes intimate mixing of the gas and aqueous phases in a countercurrent flow. Apparatus and methods for mixing gases and aqueous phases are known, and include bubbling of gas through a column of the aqueous phase, venturi-type mixers, "bubble tray" or "liquid tray" arrangements within towers that are contacted with a flow of the liquid phase or with a flow of the gas phase, respectively, and distribution of the aqueous phase as a mist or fine droplets that are carried through the gas phase or fall through it under the influence of gravity. See, for example, U.S. Pat. Nos. 2,410,583, 5,434,330, 6,111,155, 6,028,234, 6,797,039 and US20130012751, all hereby incorporated by reference in their entirety and for all purposes.

The hydrate forming reactor also comprises a series of stages, which are established by creating zones within the reactor that are controlled to a selected temperature by either refrigeration or heating as necessary. For example, in a reactor in which a flow of gas upward is contacted by a flow of aqueous phase as a falling mist, zones of defined temperature can be established by baffles perforated by riser tubes, each baffle being configured to carry a heat exchange fluid so as to control the temperature of the baffle and associated riser tubes to a selected temperature by heating or refrigeration of the heat exchange fluid. As another example, in a "tray" arrangement, the temperatures of each of the trays can be individually controlled.

A gas feed inlet to the HFR is configured to feed a gas stream into the vessel. The gas feed can be located at the first end (which can be the bottom, if the HFR is oriented vertically) of the vessel encompassing the HFR, but is typically located some distance from the first end so that a "feed stage" can be established that is somewhat distal from the first end, allowing for separation stages upstream (for the gas flow) from the gas feed inlet. The particular form of the gas feed inlet will depend upon the overall design of the HRF. For example, if a feed is bubbled into the reactor, a sparger or an arrangement of a plurality of small nozzles might be used as the gas inlet. Heating or cooling apparatus, a pump or compressor, and the like, can be incorporated into a gas feed inlet to the HFR. Control of the gas feed, including of its temperature and pressure, is considered well-known in the art.

The gas feed inlet of the HFR can be configured to include an inlet that allows for introducing a hydrate promoter into the gas phase.

An aqueous phase inlet is configured to feed an aqueous phase into the vessel. An aqueous phase inlet can include an input for fresh, "make-up" water.

The aqueous phase inlet is typically placed at the second end of the vessel that encompasses the HFR, although alternative arrangements are also envisioned in which a number of aqueous phase inlets are provided distributed along the length of the HFR proximate to the second end of the HFR. As for the gas inlet, the specific form of the aqueous phase inlet will depend on the overall design of the HFR. For example, if the counterflow of the aqueous phase is in the form of a falling mist, the aqueous phase inlet can be arranged as a plurality of fine nozzles disposed around the circumference of the top of the HFR that is oriented vertically.

The aqueous phase inlet can be configured to include a mixer for introducing an amount of one or more hydrate promoters, in either liquid or solid form, into the aqueous phase.

The aqueous phase inlet can also be configured to include a mixer for introducing one or more inorganic or organic salts or surfactants into the aqueous phase. The salt(s) may be added in solid form or as a solution. A salt solution of the aqueous phase allows chilling of the aqueous phase to temperatures below 32° F. (0° C.). Ocean water may be used as the aqueous phase.

The form of the hydrate slurry outlet(s) of the HFR is considered known in the art and again the specific form will depend on the overall design of the HFR and also to the form of the hydrate (e.g. particle size) and its concentration in the slurry.

The form of the one or more gas product outlets is also considered known in the art, and again the specific form will depend on the overall design of the HFR. The end use of the product gas will be considered in selecting the form of the gas product outlet. For instance, if the product gas is to be discharged to the atmosphere as a pure gas, a simple pressure release valve can suffice. On the other hand, if the product gas is to be used to drive a turbine, then the product gas outlet will be configured with appropriate couplings for attaching to a gas pipeline or storage vessel and to appropriate pressure controls.

A system for separating methane from ($C_2$ or) $C_{2+}$ gases in natural gas or other gas mixtures can include a plurality of HFRs arranged in series. In such an arrangement, the hydrate product from a first HFR is decomposed and the gas released from the first decomposed hydrate is used as the gas feed (which can be mixed with, e.g. a hydrate promoter as described below) into a second HFR. Such a second or yet additional HFR(s) can be operated at the same pressure and/or temperature as the first HFR, or can be operated at a reduced pressure and/or different temperature gradient or step series, compared to the pressure and temperatures in the first, or upstream HFR (e.g., 450 psia for the first of two HFRs, and 225 psia for the second of two HFRs). A measurement of the composition of gas released from the decomposed hydrate obtained from an upstream HFR or calculation of the composition of the hydrate from equilibrium principles can be used to set the composition of the input gas for calculation of the staging to be used in a respectively downstream HFR.

In an alternative arrangement, the slurry from the first HFR is transported to a second HFR for use in the aqueous phase, and different conditions of pressure and/or temperature are used in the second reactor to change the hydrate composition. Whatever gas is released during a pressure change can be combined with the methane-rich phase for storage, power generation or another industrial use.

A hydrate formation promoter can be added to either the gas stream or to the aqueous phase. Hydrate formation promoters can be of either the thermodynamic or kinetic type. A thermodynamic hydrate formation promoter ("THP") changes the equilibrium conditions for hydrate formation and will lower the pressure at which hydrates are able to form. A kinetic hydrate formation promoter ("KHP") accelerates the rate of hydrate formation without changing the equilibrium conditions. Examples of THPs include acetone, propane, isobutane, cyclopentane, carbon tetrachloride, bromoform, chloroform, ethylene dichloride, methylene chloride, methyl iodide, methylene iodide, and the tri-halogen compounds of methane and ethane, propylene oxide, 1,4-dioxane, tetrahydrofuran and $H_2S$, surfactants (e.g. TBAB—Tetra n-Butyl Ammonium Bromide, TBAF—Tetra n-Butyl Ammonium Fluoride, TBACl—Teta n-Butyl Ammonium Chloride), and enzymes (glucoamylase). Examples of KHPs include surfactants (e.g. SDS—Sodium Dodecyl Sulfate, DTAC—Dodecyl Trimethyl Ammonium Chloride) and inorganic or organic salts (e.g. NaCl).

A system for separating methane from ($C_2$ or) $C_{2+}$ gases from natural gas or other gas mixtures can further include a solid-liquid (SLS) separator configured to receive an aqueous hydrate slurry from the hydrate slurry outlet for separation into an aqueous phase product and a solid hydrate. The SLS can be integral with the HFR at the first end of the vessel. In such an instance of a SLS integral with the HFR, the hydrate slurry outlet can be replaced by an outlet suitable for conveying a solid hydrate material from the HFR and an outlet suitable for conveying an aqueous phase from the HFR. The hydrate product of the SLS can be collected and transported and/or sequestered as a concentrated hydrate product, or decomposed as described further below.

When the system includes a SLS, the system can further include an aqueous phase recirculation line that connects a reservoir or pipe of the SLS holding the recovered aqueous phase to the vessel of the HFR, typically via the aqueous phase inlet, but in some embodiments a separate inlet for the recirculating aqueous phase can be provided. Aqueous phase recovered from the hydrate separation can be recirculated back to the HFR via this line. The aqueous phase recirculation line can include a cooling plant to cool the aqueous phase prior to introducing the recycled aqueous phase back into the HFR. The aqueous phase recirculating line can alternatively or additionally include an inlet for adding a kinetic hydrate promoter to the recirculating aqueous phase.

A system for separating methane from ($C_2$ or) $C_{2+}$ gases natural gas or other mixture of gases can additionally or alternatively include a hydrate decomposition facility ("HDF"). The HDF can be operably connected directly to the hydrate slurry outlet of the HFR, or the HDF can be operably connected to receive the concentrated hydrate product (which can be in the form of a concentrated slurry or a solid) from the SLS. A HDF generally comprises a hydrate decomposition plant ("HDP") and a vapor-liquid separator ("VLS").

The hydrate decomposition plant decomposes the hydrate into its component gas(es) and an aqueous phase comprising the empty clathrate and water. The decomposition can be effected by either heating of the hydrate or reducing the pressure under which it is kept, or a combination of both. Accordingly, the HDP can contain either or both of a heater for raising the temperature of the hydrate or apparatus for lowering the pressure under which the hydrate is maintained at the outlet of the HFR or SLS.

The HDF further includes a VLS for separating a vapor product from an aqueous phase. The VLS is configured such that the vapor product of the VLS is collected and stored and/or transported for use in another industrial process. The VLS can be further configured so that the aqueous phase liquid product is returned to the vessel of the HFR via an aqueous phase recirculating line. The aqueous phase recirculating line can include a cooling plant for cooling the aqueous phase liquid product. Additionally or alternatively, the aqueous phase recirculating line can include an input for adding a hydrate promoter and/or an inorganic or organic salt to the aqueous phase.

Unless otherwise indicated, for instance by more detailed description, movement of gases and fluids, and control of their temperature and pressure, is considered known in the art. Accordingly, the flow lines, inlets and outlets described herein may be considered to include apparatus for moving and controlling the flow of fluids between and within components of the systems disclosed, such as pumps, compressors, valves of different kinds, meters, feedback controls, digital controls and the like, as one of ordinary skill in the art would expect to use.

Figure 4:
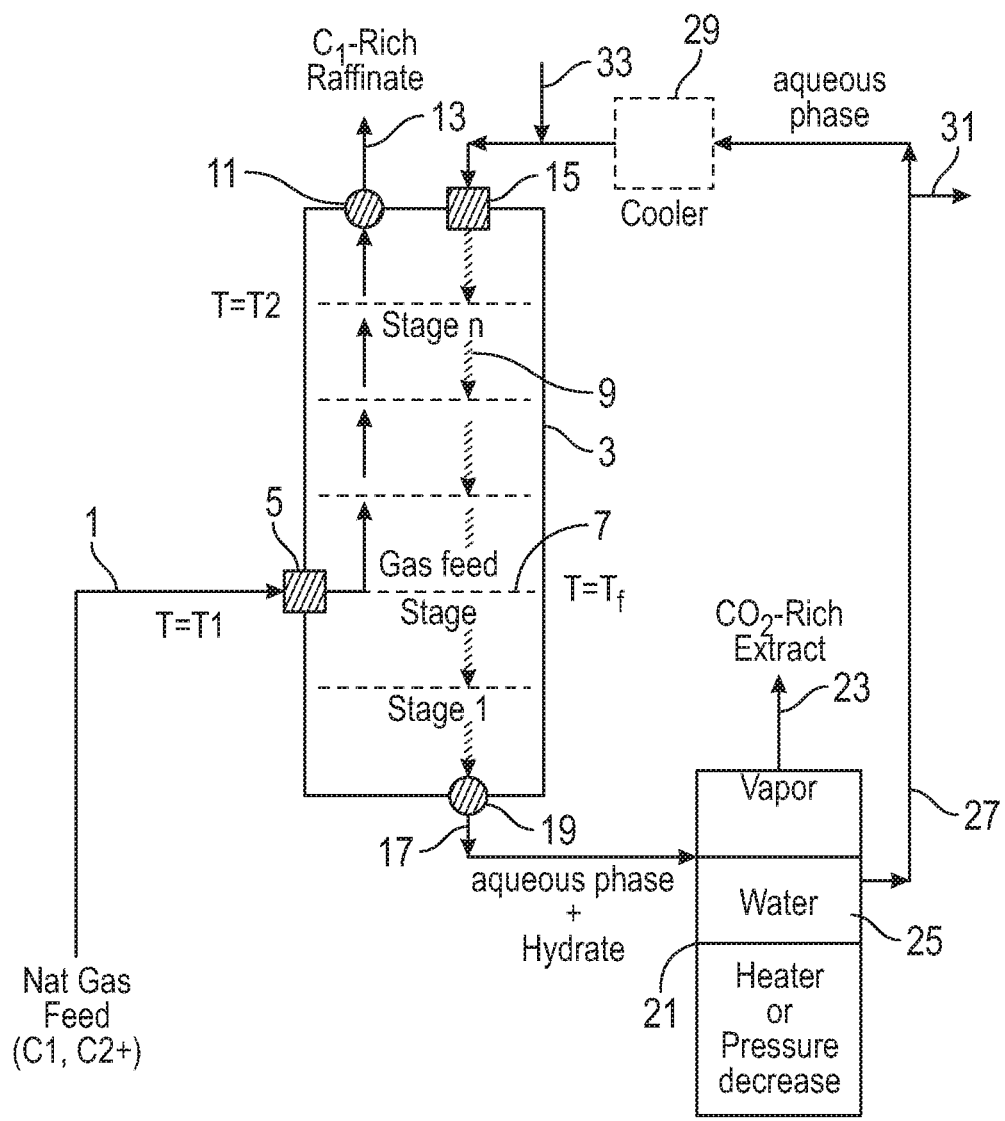
FIG. 4 is an illustration of a system for separating methane from $C_{2+}$ gas.

FIG. 4 illustrates an embodiment of a system for hydrate-based gas separation. A feed gas stream 1 enters a hydrate formation reactor (HFR) 3 via a gas inlet 5 located at a gas feed stage 7. The gas feed stage is maintained at a temperature $T_f$. The gas stream flows in countercurrent fashion in contact with an aqueous phase stream 9, through a stage n and out a product gas outlet of the HFR 11. Stage n is maintained at a temperature $T_2$. The product gas 13 is stored, put to use or vented to the atmosphere.

The aqueous phase stream enters the hydrate formation reactor via an aqueous phase inlet 15 and flows countercurrent to the gas stream and exits the hydrate formation reactor as a hydrate slurry 17 via a hydrate slurry outlet 19. The aqueous phase hydrate slurry is transported to a hydrate decomposition facility 21 that includes both a hydrate decomposition plant (HDP) and a vapor-liquid separator (VLS). The hydrate is decomposed in the HDP into the component gas(es) and the aqueous phase (water or a water solution) by operation of a heater or by lowering the pressure under which the hydrate is maintained. The resulting gas(es) and aqueous phase are separated one from another in the VLS to obtain a captured gas 23 and regenerated aqueous phase 25. The regenerated aqueous phase leaves the VLS via an aqueous phase recirculating line 27. The regenerated aqueous phase is recirculated to the HFR via the aqueous phase inlet. The aqueous phase recirculating line optionally includes a cooling plant 29 for cooling the aqueous phase. The aqueous phase recirculating line also includes a bleed 31 for drawing off portions of the aqueous phase. The aqueous phase recirculating line, and/or the aqueous phase inlet of the HFR, contains a water make-up inlet 33 for introducing fresh water into the system. The concentration of solutes in the aqueous phase can be adjusted by adding fresh water and/or removing aqueous phase via the water make-up and bleed.

The captured gas-rich hydrate can be stored or transported under conditions suitable for maintaining the hydrate for further industrial use.

Also provided is a process for purifying methane from ($C_2$ or) $C_{2+}$ gas from natural gas or other gas mixtures. The process includes contacting a feed gas stream comprising methane and $C_{2+}$ gases and a aqueous phase stream in a countercurrent flow to form a $C_{2+}$ gas-rich hydrate in the aqueous phase, a temperature $T_f$ being maintained at a gas feed stage f in the countercurrent flow, a temperature $T_2$ such that $T_2 < T_f$ being maintained at a stage n>f, and a temperature $T_1$ being maintained at a stage m≤f such that $T_1 \geq T_f$;

wherein:

$T_2$ is in the range from the incipient vapor temperature for ($C_2$ or) $C_{2+}$ to the incipient hydrate temperature for $C_{2+}$ at the operating pressure of the process, and $T_1$ is a temperature at or below a temperature of convergence of the incipient ($C_2$ or) $C_{2+}$ hydrate and incipient ($C_2$ or) $C_{2+}$ vapor curves at the operating pressure of the process.

The gas of the gas feed stream is preferably one that includes some ethane. Typically natural gas, whether directly as produced from a formation or following treatment to remove corrosive gases such as $H_2S$ and/or $CO_2$, is separated.

The methane in the gas feed is separated from at least $C_2$ or $C_{2+}$ gases and other gases by intimately contacting the gas feed stream with a stream of an aqueous phase under certain conditions of pressure and temperature in a countercurrent flow. The countercurrent flow and the conditions of temperature and pressure establish a series of "stages" in the HFR. The process is run isobarically within any one HFR, and so the stages of the separation in any one HFR are determined by variations in temperature. The equilibrium concentrations of methane and $C_2$ or $C_{2+}$ gas and other gases in each of the gas and hydrate phases change at each stage. The process can be conducted using only one stage. In such an instance, $T_f = T_1 = T_2$. Typically the process is conducted using at least two stages. In any event, the stages can be considered as a first stage at the lowest temperature in separation step, one or more up to n stages at progressively higher temperatures and a gas feed step f, which is the stage at which the gas feed inlet to the HFR is located. The gas feed stage can be at any stage. The gas feed stage is typically the first, second or third stage, most typically the second or third stage.

The design of the separation, that is determination of the overall operating pressure of the separation process, and the number of stages and their temperature can be performed using calculations from equilibrium principles, in the manner similar to the calculations for designing a distillation of a binary liquid.

Separation in the proposed multistage configuration is driven by varying operating conditions, in this instance temperature, at each stage. A single HFR system utilizes is run isobarically using different temperatures for different stages. Stages can be implemented instead as a chain of coupled HFRs, each designed to run at different pressures.

At any given operating pressure, addition of warmer stages below the gas feed stage result in improved methane recovery and $C_2$ or $C_{2+}$ purity, whereas addition of cooler stages above the gas feed stage result in improved $C_2$ or $C_{2+}$ recovery and methane purity.

For determination of the operating pressure of the process, the feed gas composition is located along the x-axis of a plot of composition (as mole fraction) vs. incipient hydrate formation pressure for a methane-ethane binary gas. Natural gas typically has a composition comprising from about 95 mol % methane and about 5 mol % other gases, substantially ethane, but also minor amounts of other gases (ethene, propane, butanes, pentanes, $H_2S$, $CO_2$), to about 25 mol % methane and about 75 mol % other gases, substantially $CO_2$. For example, natural gas can have a composition of 26 mol % CH4 and 71 mol % $CO_2$.

As shown in FIG. 1, (showing only a binary mixture of methane and ethane) the operating pressure of the process is at least about 450 psia) at 40° F. (4.4° C.).

Figure 2:
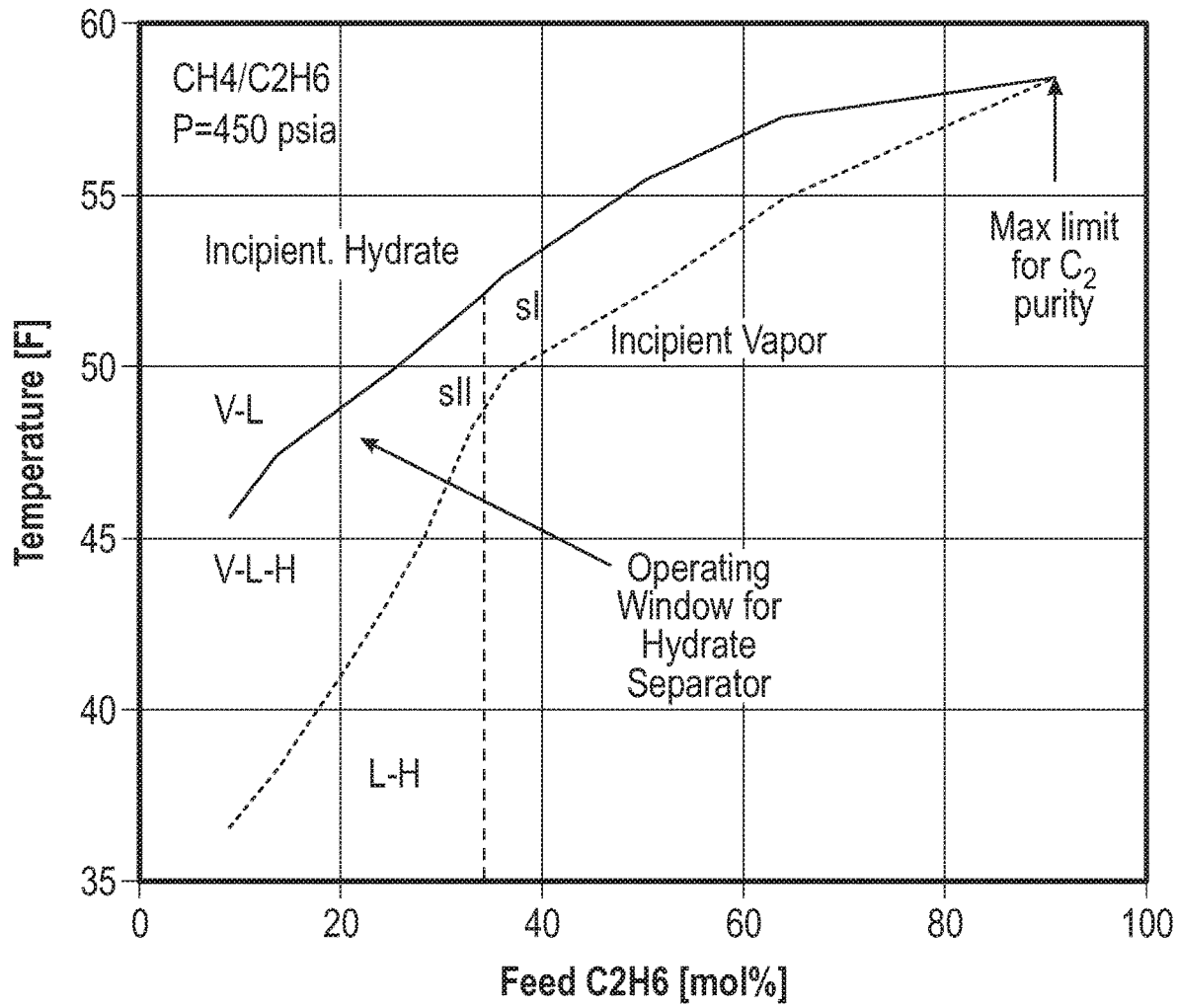
FIG. 2 is a phase diagram for hydrate formation at 450 psia as a plot of incipient hydrate formation pressure vs. temperature for a gas feed having component ratios from 9 moles methane:1 mole ethane to 1 mole methane:9 moles ethane.

A phase diagram (composition as mol % vs. temperature), similar to a boiling point diagram of a binary liquid mixture, can then be calculated for the vapor-liquid (V-L), vapor-liquid-hydrate (V-L-H) and liquid-hydrate (L-H) phases of the binary mixture at the selected pressure. FIG. 2 shows the calculated phase diagram of an ethane/methane binary mixture at 450 psia. Staging for the separation can then be derived either from a McCabe-Thiele plot of the equilibrium composition of vapor and hydrate at a desired pressure (typically the lowest pressure, or nearly so, that provides for hydrate formation of the feed gas composition), and then observing the temperatures at the incipient hydrate formation curve at the composition indicated for each of the stages.

Alternatively, staging can be designed by calculating phase diagrams for vapor-liquid (v-l), vapor-liquid-hydrate (v-l-h) and liquid-hydrate (l-h) phase diagrams for a feed gas composition, of the two gases to be separated (methane and ethane, for example, as below) for mol % of one of the gases to be separated from the feed gas vs. temperature at a given pressure. A temperature for the first stage can be selected by picking a temperature between the equilibrium incipient hydrate formation curve and incipient vapor formation curve at the composition desired in the hydrate phase. A temperature of the last stage is then selected by picking the temperature on the incipient vapor formation curve at the composition desired in the gas captured in the hydrate. Temperatures of intermediate phases, if any, are then identified by noting the composition of the incipient vapor at the temperature selected for the first stage, then noting the temperature of the incipient hydrate formation curve at this composition as the temperature for the second stage. The temperature of the third stage is selected by noting the composition at the incipient vapor formation line at the temperature of the second stage, then noting the temperature of the incipient hydrate formation line at this composition, etc.

Figure 5:
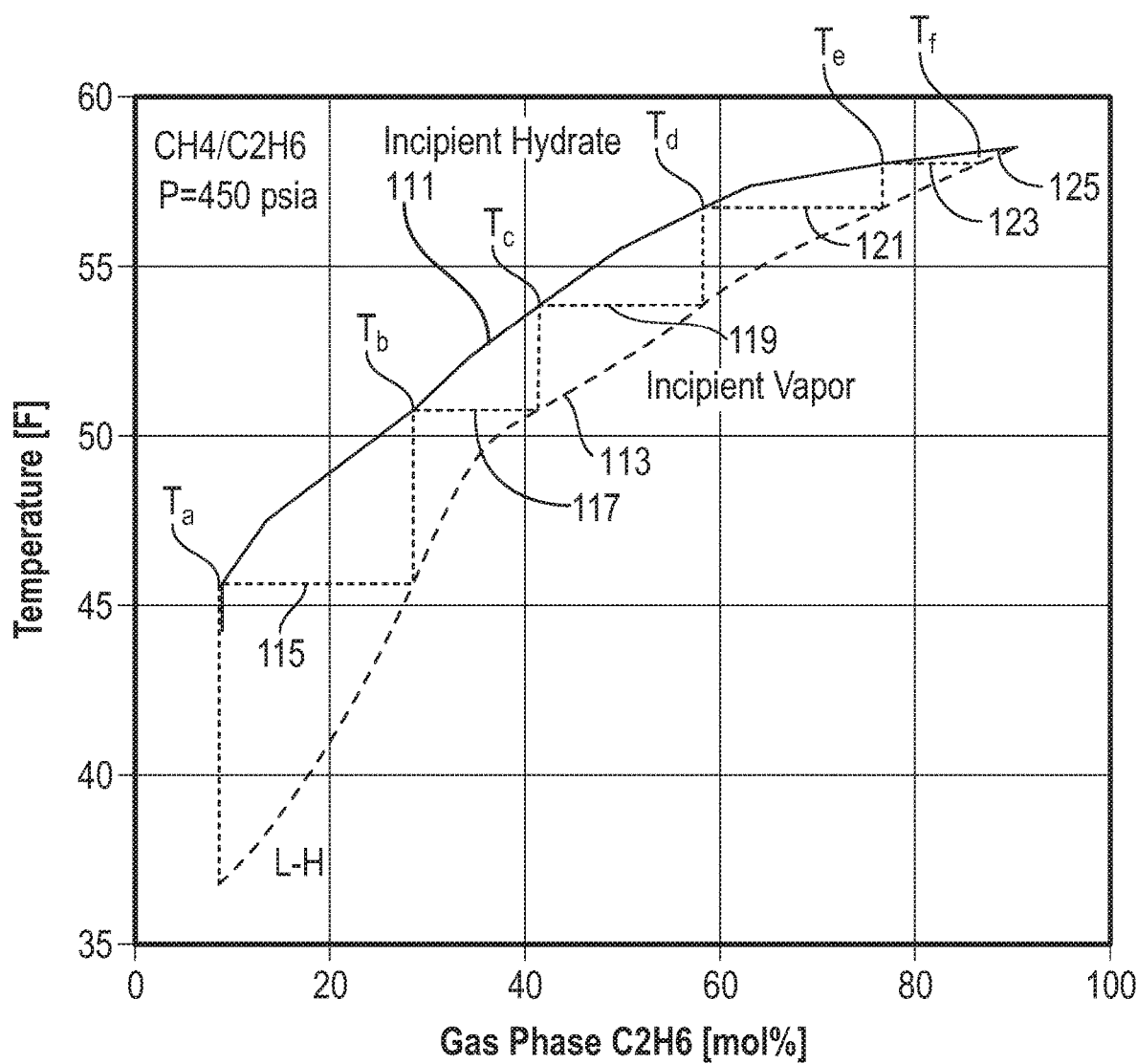
FIG. 5 illustrates a determination of staging in a methane separating process.

FIG. 5 illustrates the determination of staging in the separation using the equilibrium curves as described above. A phase diagram for a gas binary mixture is calculated from equilibrium principles at a selected operating pressure to generate an incipient hydrate formation curve 111 and an incipient vapor formation curve 113. The plot is of temperature vs. composition (in mol %) of the binary mixture, similarly as a "boiling point" diagram used to design a distillation process. In FIG. 5, the mixture is of methane and ethane and the pressure is 450 psia. A composition for the gas feed is chosen, and then a temperature in the range between the incipient hydrate formation curve 111 and an incipient vapor formation curve incipient hydrate formation curve and an incipient vapor formation curve is selected for the first stage temperature ($T_a$, in this instance 46° F.). A first "operating line" 115 is drawn at the temperature to the incipient vapor formation line. The intersection provides the composition of the gas at the next stage. The temperature at that composition shown on the incipient hydrate formation curve provides the temperature ($T_b$) of the next stage. A second operating line 117 is drawn to determine the composition of the gas at the next stage, which is in turn used to find the temperature for the next stage ($T_c$) at a third operating line 119. The iteration continues to identify a fourth temperature ($T_d$) at a fourth operating line 121, a fifth temperature ($T_e$) at a fourth operating line 123, a sixth temperature ($T_f$) at a fifth operating line 125. A separation run in accord with this design is expected to provide purification of methane/ethane mixture of 10 mol % ethane/90 mol % methane to a composition of 90 mol % ethane/10 mol % methane.

We have developed a computational model of the hydrate-based separation process. The model includes a combination of hydrate formation thermodynamics and the multistage countercurrent operation, and generates results from these known principles. See, e.g. E. Dendy Sloan Jr. and C. Koh, "Clathrate Hydrates of Natural Gases", Third Edition, CRC Press, 2007 and A. L. Ballard and E. Dendy Sloan Jr., "The next generation of hydrate prediction: An overview", *Journal of Supramolecular Chemistry*, vol. 2, pp. 385-392 (2002). Both of these references are hereby incorporated by reference in their entirety and for all purposes. The integrated model takes as inputs feed composition and operating conditions and iteratively generates phase fractions and compositions as outputs.

A process for separating methane from a gas mixture comprising ($C_2$ or) $C_{2+}$ gases can further include separating the gas stream from the aqueous phase after the contacting step and collecting a hydrate slurry formed in the aqueous phase and comprising hydrate particles enriched in ($C_2$ or) $C_{2+}$ gases. A process can further include concentrating the hydrate from the hydrate slurry. The collecting and concentrating can be effected by a solid-liquid separator. The solid-liquid separator may, for example, include a device such as a conveyor belt or spinning drum separator. In other embodiments, the hydrate may be separated by falling through a tower, e.g. as described in US20130012751, hereby incorporated by reference.

The separated hydrate can also be stored and/or transported under conditions sufficient to maintain the hydrate for use in a further industrial process or as fuel. Alternatively, the hydrate can be decomposed, by increasing the temperature at which it is maintained, by decreasing the pressure at which it is maintained, or by a combination of both.

The $C_2$-rich or $C_{2+}$-rich gas released by the hydrate decomposition ("captured gas") can then be transported for use in a further industrial process or burned as fuel. Alternatively, the captured gas can be used as a feed into an iteration of the separation process that is run under conditions appropriate to the input captured gas composition.

Additionally or alternatively, the product gas of the separation, for example a methane-rich gas, can be collected after the step of contacting the gas with the aqueous phase. The collected product gas can be stored under a pressure above atmospheric pressure or transported under pressure to be used for fuel or as an input substance to an industrial process.

In some implementations of a separation of methane from $C_2$ or $C_{2+}$ from a gas mixture, the process is conducted at 450 psia, $T_2$ is from 36 to 46° F. (2.2 to 7.8° C.) and $T_1$ is about 59° F. (15° C.). In some implementations of a separation of methane from $C_2$ or $C_{2+}$ from a gas mixture the process is one in which there are 5, 6, 7 or 8 stages and $T_f$=40° F. (4.4° C.). The process can be one in which:
  i) there are 5 stages, f=4, and the temperature
    a) of stage 1 is about 51° F. (10.6° C.);
    b) of stage 2 is about 49° F. (9.4° C.);
    c) of stage 3 is about 46° F. (7.8° C.);
    d) of stage 4 is about 40° F. (4.4° C.);
    e) of stage 5 is about 38° F. (3.3° C.); or
  ii) there are 6 stages, f=5, and the temperature
    a) of stage 1 is about 55° F. (12.8° C.);
    b) of stage 2 is about 51° F. (10.6° C.);
    c) of stage 3 is about 49° F. (9.4° C.);
    d) of stage 4 is about 46° F. (7.8° C.);

e) of stage 5 is about 40° F. (4.4° C.);
f) of stage 6 is about 38° F. (3.3° C.); or
iii) there are 7 stages, f=5, and the temperature
  a) of stage 1 is about 55° F. (12.8° C.);
  b) of stage 2 is about 51° F. (10.6° C.);
  c) of stage 3 is about 49° F. (9.4° C.);
  d) of stage 4 is about 46° F. (7.8° C.);
  e) of stage 5 is about 40° F. (4.4° C.);
  f) of stage 6 is about 38° F. (3.3° C.);
  g) of stage 7 is about 36° F. (2.2° C.); or
iv) there are 8 stages, f=6, and the temperature
  a) of stage 1 is about 56° F. (13.3° C.);
  b) of stage 2 is about 55° F. (12.8° C.);
  c) of stage 3 is about 51° F. (10.6° C.);
  d) of stage 4 is about 49° F. (9.4° C.);
  e) of stage 5 is about 46° F. (7.8° C.);
  f) of stage 6 is about 40° F. (4.4° C.);
  g) of stage 7 is about 38° F. (3.3° C.); and
  h) of stage 8 is about 36° F. (2.2° C.).

In any embodiment of the process, the feed gas stream can include a hydrate promoter. Additionally or alternatively, in any embodiment of the process, the aqueous phase stream can include a hydrate promoter.

Figure 6:
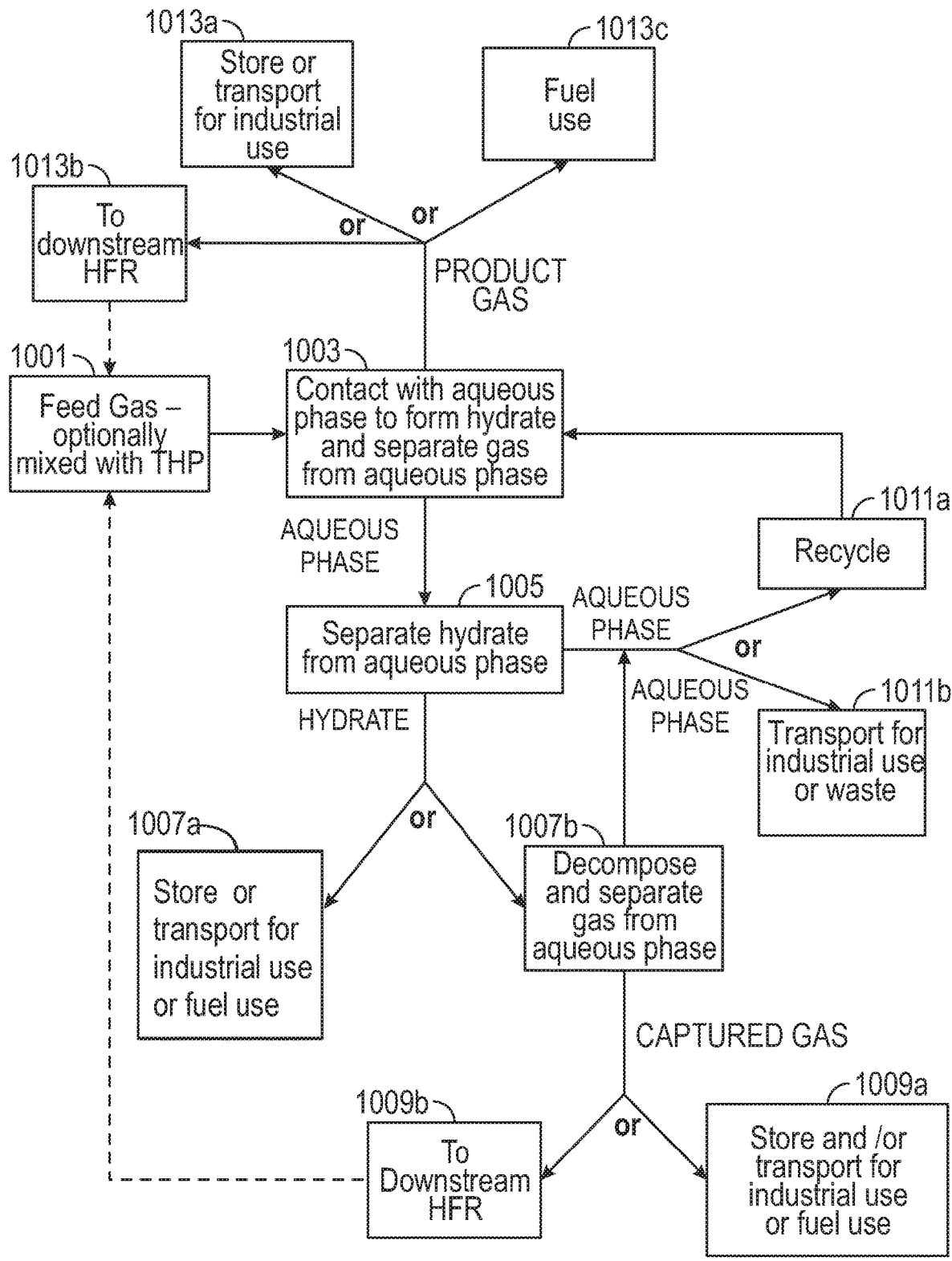
FIG. 6 shows a flow chart for a process for separating methane from $C_{2+}$ gases.

FIG. 6 illustrates the flow of the disclosed process. At 1001, a feed gas is provided in a gas stream that at 1003 is contacted with an aqueous phase stream to form a hydrate in the aqueous phase stream, and the gas stream and aqueous phase stream are separated one from the other. At 1005, the hydrate is separated from the aqueous phase and at 1007 is stored or transported for use in another industrial process (1007a), or decomposed and separated into its component gas(es) and aqueous phase (1007b). At 1009, the gas obtained from decomposition of the hydrate is stored for transport or used directly in a further industrial (1009a), or used as a feed to a downstream iteration of the process (1009b).

At 1011, the aqueous phase obtained from the hydrate separation can be recycled to the countercurrent flow (1011a) or transported for further industrial use or sent to waste (1011b).

At 1013, the gas product of the countercurrent separation is collected and stored or transported for further industrial use (1013a), used as a feed to a downstream iteration of the process above (1013b), or stored or transported under pressure for use as fuel (1013c).

EXAMPLES

The following examples of gas separations are intended to be illustrative only and not limiting of the scope of the invention, which is defined solely by the claims following.

Example separations of methane from mixtures with $C_2$ or $C_{2+}$ gases are simulated by a computational model. The model includes a combination of hydrate formation thermodynamics and multistage countercurrent tower operation. The integrated model takes as inputs feed composition and operating conditions and iteratively generates phase fractions and compositions as outputs.

Example 1: Pressure Requirement for Hydrate Formation

As a first step to study the methane-ethane system, simulations are used to estimate the minimum pressure required for hydrate formation. FIG. 1 shows the minimum pressure requirement as a function of ethane mole fraction in the feed gas. As the feed becomes dilute in ethane, the pressure requirement for hydrate formation increases exponentially. The instance of a natural gas comprising about 95 mol % methane, 5 mol % ethane is shown, and a requirement for a modest minimum pressure (~377 psia) to obtain hydrate formation is found.

The minimum pressure requirement for feeds containing higher concentrations of ethane are even lower. For example, for a feed containing 90 mol % methane and 10 mol % ethane, the minimum pressure required for hydrate formation is 309 psia. Thus, in a process using the gas product of a first HFR as the feed gas of a second HFR, the second HFR can be run at a lower pressure, and perhaps higher temperature for the hydrate formation-based process.

Example 2: Operating Temperature Window

To determine the temperature range for a separation at a fixed pressure, simulations are conducted at various methane/ethane feed compositions and a selected pressure. FIG. 2 shows the complete operating temperature window at a fixed pressure of 450 psia. The incipient hydrate curve indicates the temperature below which the hydrate phase exists (i.e., the maximum allowed temperature for hydrate formation). The incipient vapor curve indicates the temperature below which there is no vapor phase. The available operating window for the separation is the region between these two curves. Convergence of the two curves at ~90% indicates the maximum $C_2$ purity that can be achieved using multiple stages.

Example 3: Process Modeling of the Methane-Ethane System

Our process model conducts the thermodynamic calculations for equilibria at every stage, and iteratively converges the system of equations that describe a countercurrent equilibrium separation. At each stage of a multistage separation, feed composition and operating conditions are used to estimate the thermodynamic equilibrium-based phase fractions and composition.

Figure 7:
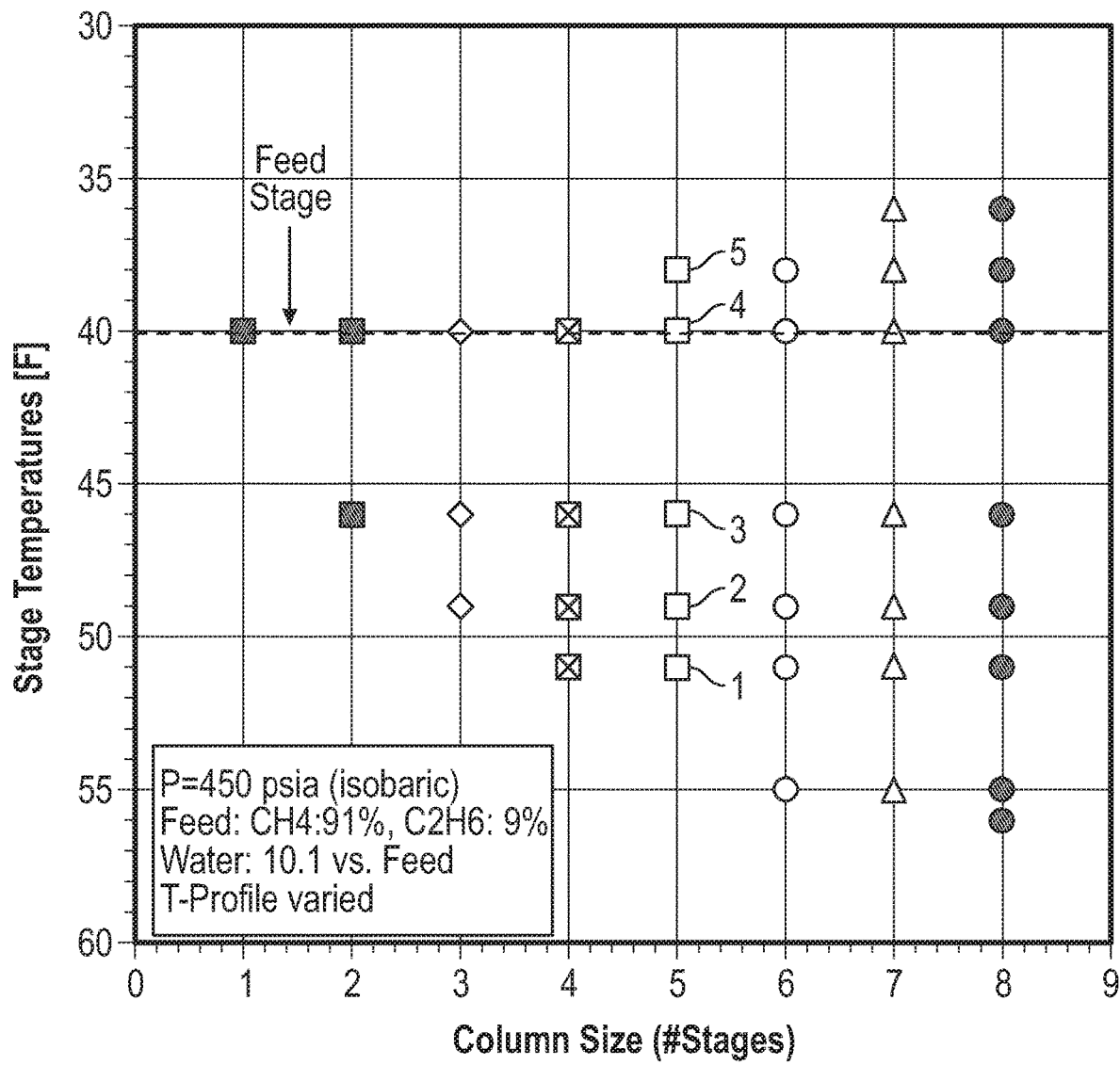
FIG. 7 illustrates the staging arrangements used in the examples.

With this generalized model, we are able to evaluate single stage and multi-stage, counter-current configurations for separation performance in terms of recovery and purity. FIG. 7 shows the staging for various simulations of methane-ethane separations using a variety of staging configurations. In all instances, the feed stage is maintained at 40° F. Simulations of processes utilizing 1 to 8 stages are performed. The feed contains 91% $C_1$, 9% $C_2$, corresponding to a typical natural gas and excess water. The pressure is fixed at 450 psia.

TABLE 1

Representative performance of a multistage hydrate-based countercurrent separator.

| Number of Stages | Ethane Purity in $C_2$-Rich Hydrate Product | Methane Purity in $C_1$-Rich Gas Product |
|---|---|---|
| Feed | 9.0 mol % | 91.0 mol % |
| 1 | 18.5 mol % | 97.4 mol % |
| 2 | 30.2 mol % | 97.4 mol % |
| 8 | 72.9 mol % | 99.3 mol % |

An isothermal single stage unit would only achieve 18.5% ethane purity; on the other hand, an 8-stage separator can achieve 72.9% ethane purity with very high recovery. A highly pure $C_1$ stream (99.3%) can be recovered at the top. $C_2$ is captured in the hydrate phase, which can be decomposed to extract it in the gas phase. Captured $C_2$ stream has a high purity (72.9%), which is a substantial improvement over the feed $C_2$ purity (9%).

Figure 8:
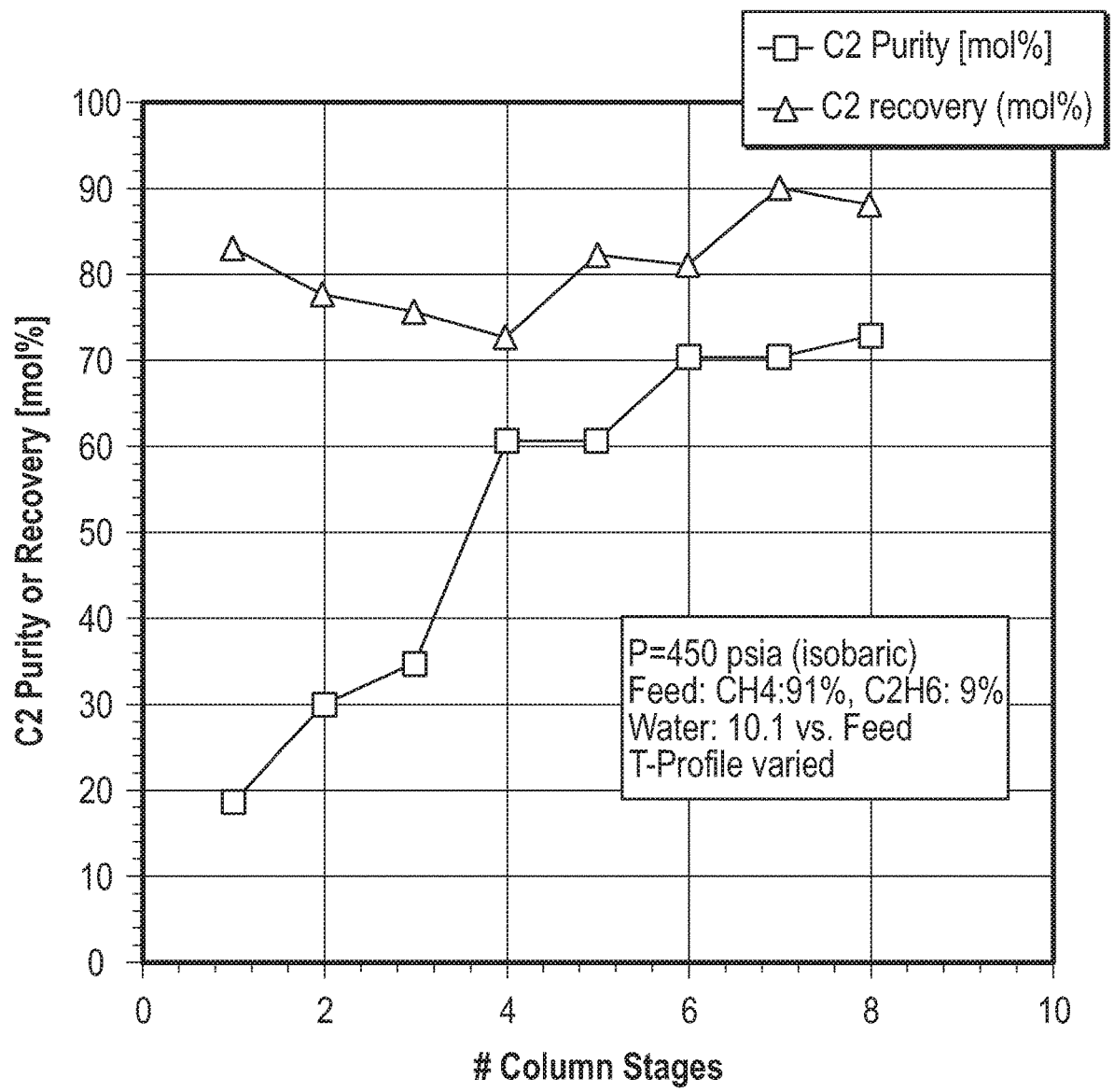
FIG. 8 illustrates how different staging arrangements affect $C_2$ gas purity and recovery.

FIG. 8 shows the results of the simulations for purity and recovery of $C_{2+}$ gases captured in the hydrate phase for each of the staging schemes in FIG. 7.

Figure 9:
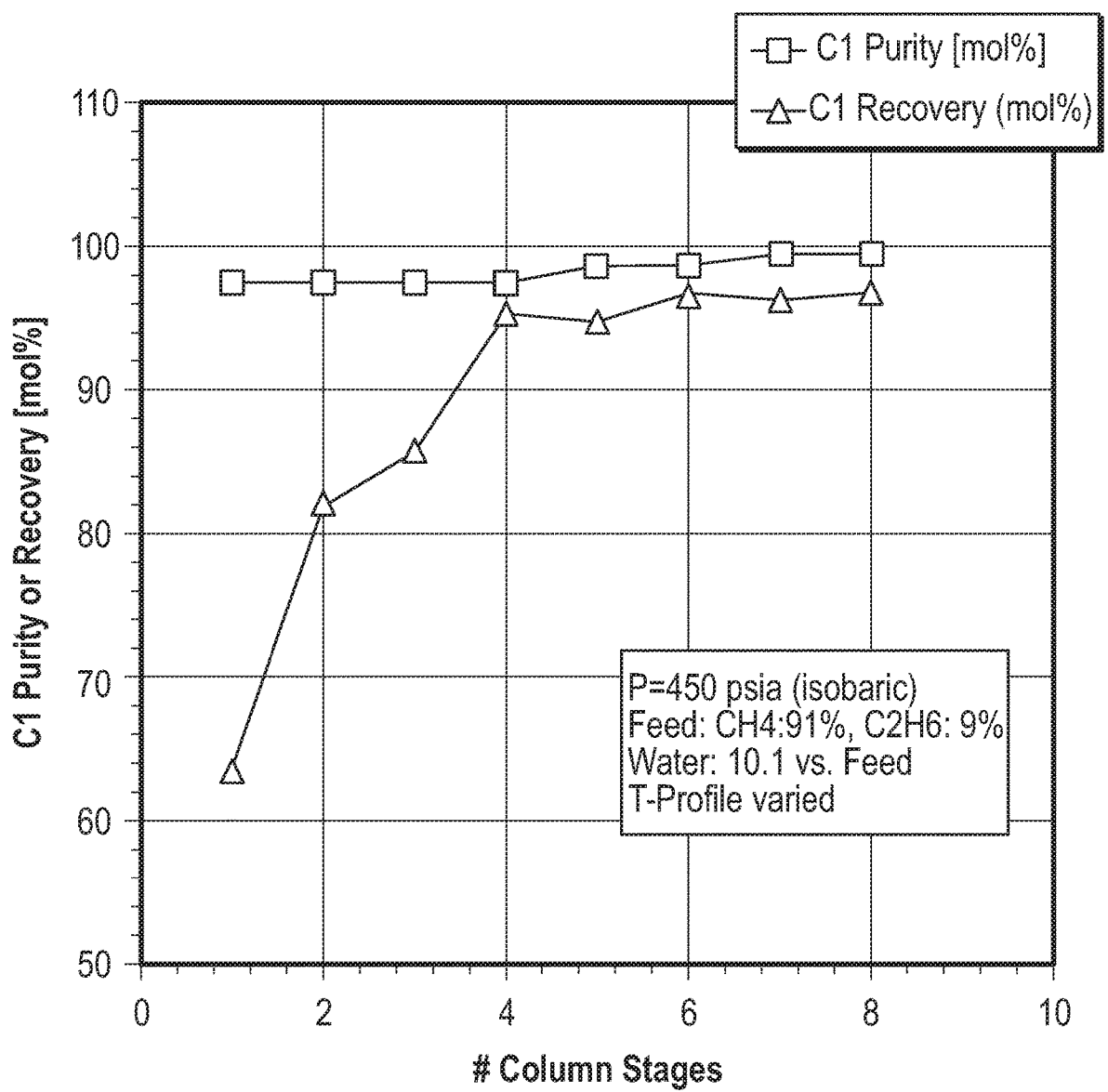
FIG. 9 illustrates how different staging arrangements affect methane purity and recovery.

FIG. 9 shows the results of the simulations for purity and recovery of methane as the product gas for each of the staging schemes in FIG. 7.

The simulations of Example 3 demonstrate that:

A multistage countercurrent configuration is able to achieve high recovery while maintaining high purity for both methane and $C_2$ or $C_{2+}$ in the vapor and hydrate phases, respectively.

The temperature profile across the stages influences purity and recovery. Colder stages above the feed stage result in improved methane purity and $C_2$ or $C_{2+}$ recovery, whereas warmer stages below the feed stage result in improved $C_2$ or $C_{2+}$ purity and methane recovery.

$C_2$ or $C_{2+}$ captured in the hydrate phase could be utilized in chemical processes such as oxidative dehydrogenation to form ethylene or methane pyrolysis.

A very pure methane gas stream (99.3%), can be obtained, which can be utilized in chemical processes such as oxidative coupling of methane to form ethylene.

The operating pressure for $C_2$ or $C_{2+}$ hydrate formation can be decreased by the other components in natural gas (e.g., $CO_2$, $H_2S$, propane, isobutane) or with additives.

Water used in the hydrate separation column can be recycled back to the start of the process after recovery of the hydrate-forming gases.

Example 4: Separation of Methane from Other Natural Gas Component Gases

Figure 10:
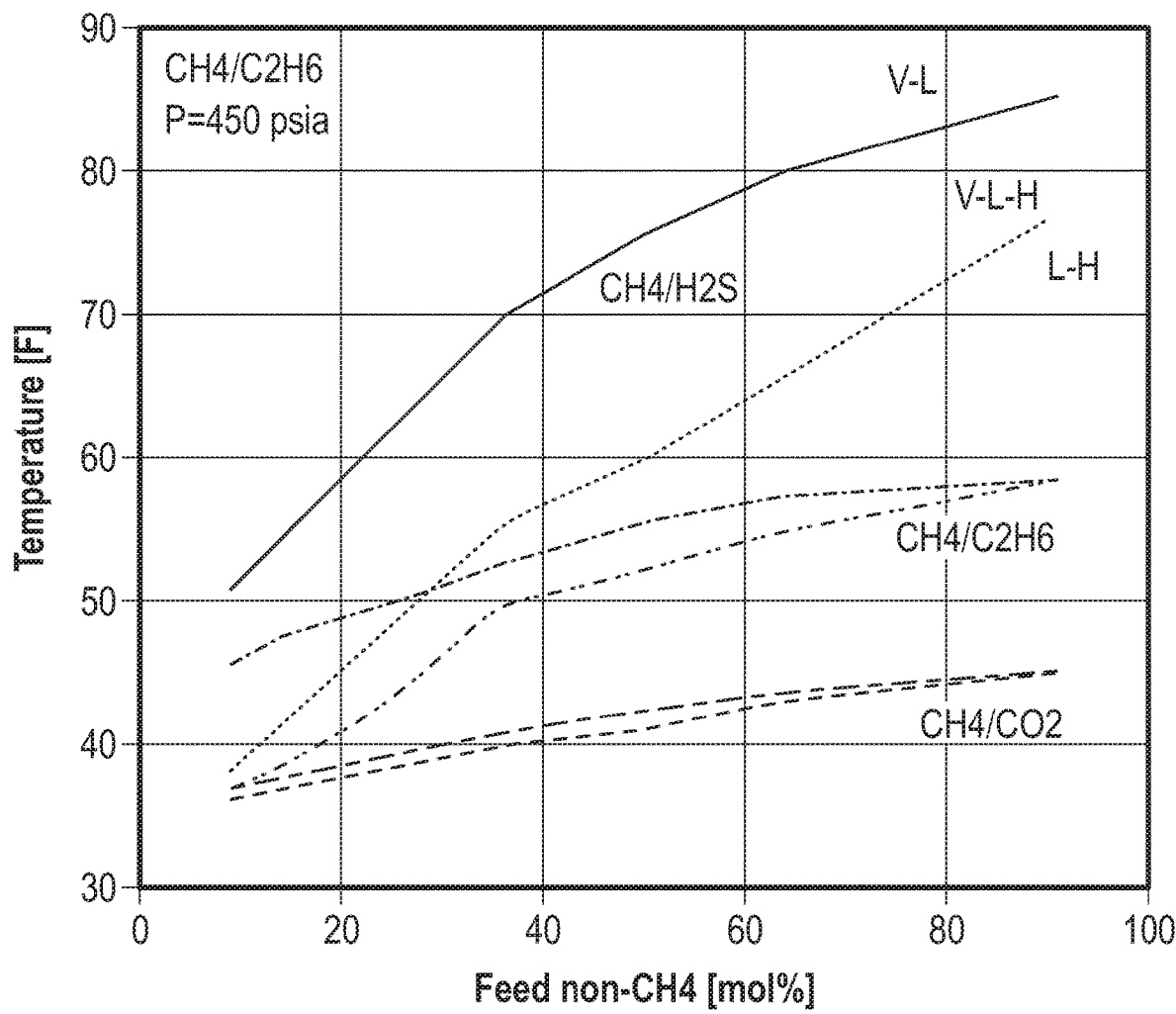
FIG. 10 shows hydrate formation phase diagrams for hydrate-based separations of methane from $H_2S$, methane from ethane, and methane from $CO_2$.

Simulations are run for separations of methane from $H_2S$ and $CO_2$ and the operating windows for these at 450 psia are compared in FIG. 10. Similar improvement can be obtained for separating other natural gas components such as propane, butane, isobutane, $H_2S$ and $CO_2$ from methane. In particular, separation of $H_2S$ from methane is significantly easier than methane-ethane separation, as the operating range for separation is much wider and close to ambient temperature conditions (see FIG. 10).

Figure 11:
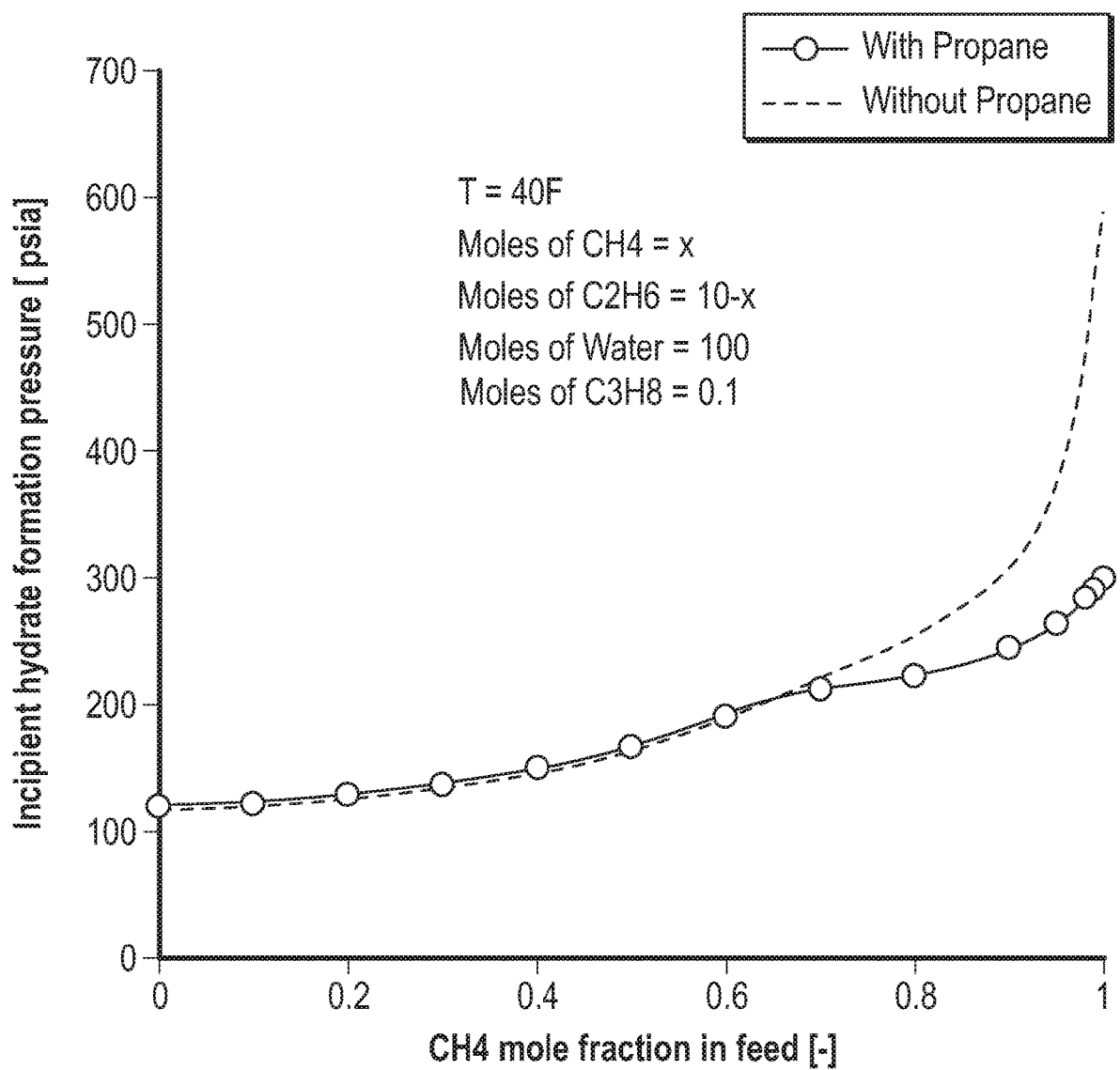
FIG. 11 shows the effect of addition of a small amount of propane to the feed gas on the incipient hydrate formation pressure for a separation of methane from ethane, i.e. a comparison of separation of methane from a mixture of methane and $C_2$ gas with separation of methane from a mixture of methane and a $C_{2+}$ gas. Propane is a natural constituent of natural gas.
Figure 12:
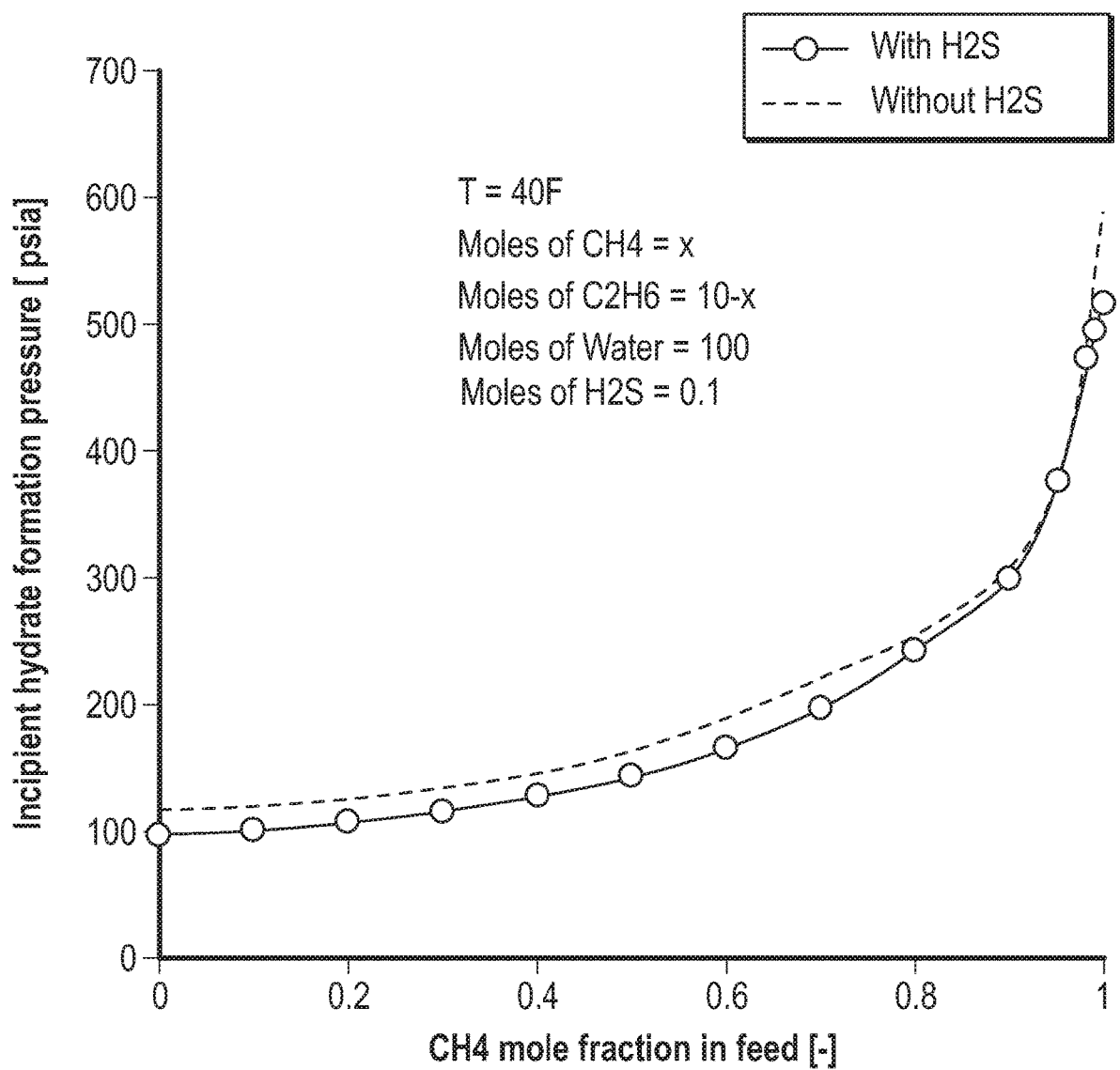
FIG. 12 shows the effect of addition of a small amount of $H_2S$ to the feed gas on the incipient hydrate formation pressure for a separation of methane from ethane.
Figure 13:
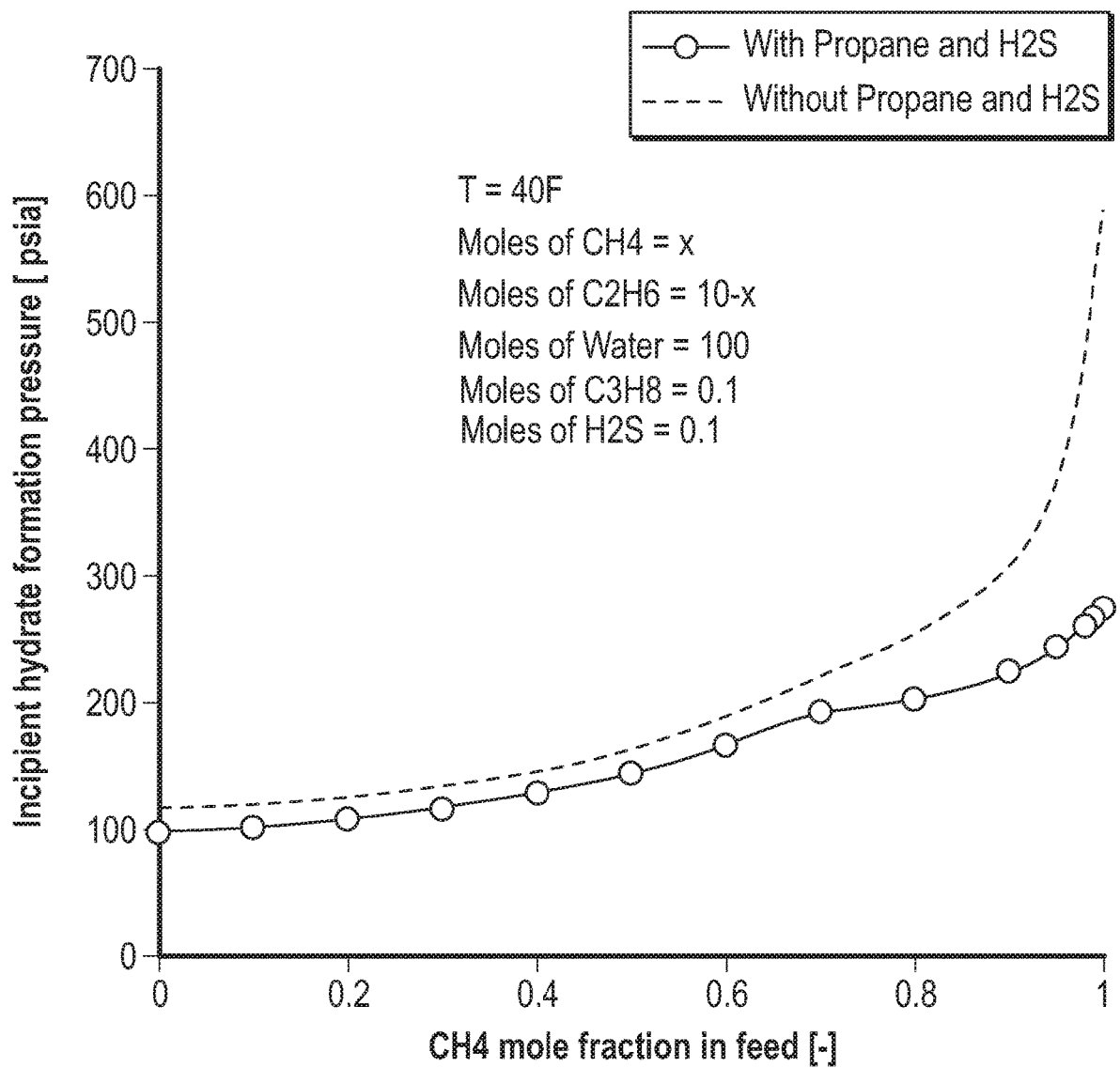
FIG. 13 shows the effect of addition of a small amount of both of propane and $H_2S$ to the feed gas on the incipient hydrate formation pressure for a separation of methane from ethane.

Example 5: Effect of Inclusion of Additional Gases in the Methane-Ethane Mixture on the Minimum Effective Operating Pressure Simulations are run to show the effect of inclusion of minor amounts of propane (FIG. 11) or $H_2S$ (FIG. 12) or both (FIG. 13) in the feed gas on separations of methane from ethane. Addition of either gas slightly lowers the minimum effective operating pressure for the separation. Addition of both gases results in an additive effect of the addition of propane and the addition of $H_2S$, albeit at different composition ranges.

The invention claimed is:

1. A system for separation of $C_1$ gas from at least $C_{2+}$ gas comprising a hydrate formation reactor (HFR) that comprises an outer container configured:

with a plurality of stages arranged with a first stage proximal a first end of the container and second and any subsequent stages successively more proximal a second end of the container;

one or more gas feed inlets placed at a distance distal from the first end of the container the same as said distance of a stage that is a second or subsequent stage and configured to feed a gas stream into the container;

one or more aqueous solution inlets configured to feed an aqueous solution stream into the second end of the container or proximate thereto;

one or more hydrate slurry outlet configured to permit a draw off a hydrate slurry stream from the first end of the container or proximate thereto;

one or more gas or liquid product outlets configured to draw off a gas or liquid product stream, respectively, from the second end of the container or proximate thereto; and a temperature control system, within the outer container, effective to establish a temperature ramp from a first temperature $T_1$ in a region proximate to the first end of the container to a second temperature $T_2$ in a region proximate to the second end of the container, wherein $T_1 > T_2$;

wherein the gas stream and the aqueous solution stream are arranged to flow in a countercurrent manner through the container.

2. The system of claim 1 that further comprises a solid-liquid separator configured to receive an aqueous hydrate slurry from the hydrate slurry outlet for separation into an aqueous phase product and a solid hydrate.

3. The system of claim 2 in which the solid-liquid separator comprises an aqueous phase recirculating line that feeds the aqueous phase product of the solid-liquid separator into the container.

4. The system of claim 3 in which the recirculating line includes a cooling plant for cooling the aqueous phase liquid product.

5. The system of claim 1 that further comprises a hydrate decomposition facility including a hydrate decomposition plant for decomposing a hydrate and a vapor-liquid separator for separating a vapor product from an aqueous phase and that is operably connected to the hydrate formation reactor so as to receive a hydrate slurry from the hydrate slurry outlet of the hydrate formation reactor.

6. The system of claim 5, in which the hydrate decomposition plant comprises a heater for raising the temperature of the hydrate.

7. The system of system of claim 5, in which the hydrate decomposition plant is one that lowers the pressure of a hydrate slurry.

8. The system of claim 5, that further comprises an aqueous phase recirculating line that feeds the aqueous phase product of the vapor-liquid separator into the container.

9. The system of claim 8, in which the aqueous phase recirculating line includes a cooling plant for cooling the aqueous phase liquid product.

10. The system of claim 1 that further comprises a gas feed mixer for adding a hydrate promoter to the gas feed stream.

11. The system of claim 2 that further comprises a gas feed mixer for adding a hydrate promoter to the gas feed stream.

12. The system of claim 8 that further comprises a gas feed mixer for adding a hydrate promoter to the gas feed stream.

13. The system of claim 3, wherein the aqueous phase recirculating line includes an input for adding a hydrate promoter to the aqueous phase.

14. The system of claim 8, wherein the aqueous phase recirculating line includes an input for adding a hydrate promoter to the aqueous phase.

15. The system of claim 12, wherein the aqueous phase recirculating line includes an input for adding a hydrate promoter to the aqueous phase.

16. The system of claim 13 that further comprises a gas feed mixer for adding a hydrate promoter to the gas feed stream.

17. The system of claim 1, in which the product gas outlet(s) are configured to transport the product gas to a storage facility for storing the product gas at a pressure above atmospheric pressure.

* * * * *